United States Patent
Luo et al.

(10) Patent No.: US 6,872,222 B2
(45) Date of Patent: Mar. 29, 2005

(54) SYSTEM AND METHOD FOR INSULATING SKIN FROM INTRAVASCULAR HEAT EXCHANGE CATHETER

(75) Inventors: Xia Luo, Buena Park, CA (US); Lynn Miyeko Shimada, Orange, CA (US)

(73) Assignee: Alsius Corporation, Irvine, CA (US)

( * ) Notice: Subject to any disclaimer, the term of this patent is extended or adjusted under 35 U.S.C. 154(b) by 133 days.

(21) Appl. No.: 10/440,867

(22) Filed: May 19, 2003

(65) Prior Publication Data

US 2004/0236394 A1 Nov. 25, 2004

(51) Int. Cl.⁷ .................................................. A61F 7/00
(52) U.S. Cl. ....................................... 607/105; 607/106
(58) Field of Search .............................. 607/96, 98–102, 607/104–106

(56) References Cited

U.S. PATENT DOCUMENTS 6,428,563 B1 * 8/2002 Keller ......................... 607/105
2002/0169489 A1 * 11/2002 Dobak, III et al. ......... 607/105

* cited by examiner

*Primary Examiner*—Roy D. Gibson
(74) *Attorney, Agent, or Firm*—John L. Rogitz

(57) ABSTRACT

Insulating foam or other material is disposed between an intravascular heat exchange catheter and the skin of a patient to alleviate patient discomfort arising from the catheter being hotter or colder than skin temperature.

11 Claims, 1 Drawing Sheet

SYSTEM AND METHOD FOR INSULATING SKIN FROM INTRAVASCULAR HEAT EXCHANGE CATHETER

I. FIELD OF THE INVENTION

The invention relates to intravascular catheters that can be used to control patient temperature.

II. BACKGROUND OF THE INVENTION

Intravascular catheters have been introduced for controlling patient temperature. Typically, a coolant such as saline is circulated through an intravascular heat exchange catheter, which is positioned in the patient's bloodstream, to cool or heat the blood as appropriate for the patient's condition. The coolant is warmed or cooled by a computer-controlled heat exchanger that is external to the patient and that is in fluid communication with the catheter.

For example, intravascular heat exchange catheters can be used to combat potentially harmful fever in patients suffering from neurological and cardiac conditions such as stroke, subarachnoid hemorrhage, intracerebral hemorrhage, cardiac arrest, and acute myocardial infarction, or to induce therapeutic hypothermia in such patients. Further, such catheters can be used to rewarm patients after, e.g., cardiac surgery or for other reasons. Intravascular catheters afford advantages over external methods of cooling and warming, including more precise temperature control and more convenience on the part of medical personnel.

The following U.S. patents, all of which are incorporated herein by reference, disclose various intravascular catheters/systems/methods: U.S. Pat. Nos. 6,419,643, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559.

SUMMARY OF THE INVENTION

A system includes a closed loop heat exchange catheter that is configured for intravascular heat exchange with a human patient. A source of heat exchange fluid is in communication with the catheter, and an insulator is configured for disposition between the catheter and the skin of the patient when the catheter is disposed in the vasculature of the patient.

The preferred insulator is made of a sheet of thermally insulating material such as, e.g., closed cell foam, paper, plastic, and fibrous materials. In the preferred embodiment, the insulator is in a substantially cylindrical configuration when it is disposed between the catheter and the patient, and the system further includes a holder engaged with the insulator for holding the insulator in the substantially cylindrical configuration.

In another aspect, a method for treating a patient includes advancing a closed loop heat exchange catheter into the patient, and effecting heat exchange between the catheter and the patient. The method also includes thermally insulating the catheter from the patient's skin.

In still another aspect, a system includes closed loop heat exchange means configured for placement in the vasculature of a patient to exchange heat with blood flowing in the vasculature. The system also includes insulating means for thermally insulating the catheter from the skin of the patient.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
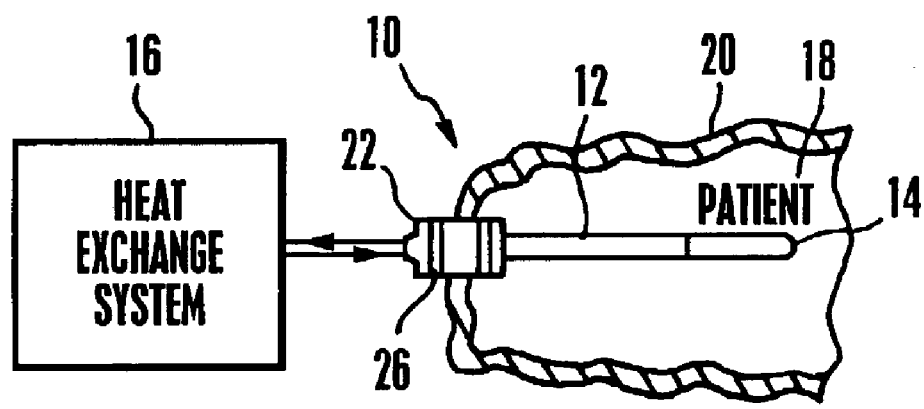
FIG. 1 is a schematic view of the present closed loop catheter system.

FIG. 1 shows an intravascular heat exchange catheter system generally designated 10 that includes a tubular catheter body 12 and a distal segment 14 that establishes a heat exchange element. Coolant such as but not limited to saline is circulated through the catheter body 12 in a closed loop to and from a heat exchange system 16 through a fluid circuit to heat or cool the coolant as desired to warm or cool a patient 18. The catheter body 12 is made of biocompatible material that may be coated with an anti-coagulant substance such as Heperin®. Preferably, the catheter body 12 is made of flexible plastic, with the heat exchange element 14 being made of inflatable and deflatable medical balloon material, although the present heat exchange element principles apply to, e.g., metal structures as well.

In any case, the catheter body 12 is sized to fit within the patient's vasculature without blocking blood flow and without allowing coolant to enter the bloodstream. The blood can flow around substantially all of the exposed surface areas of the heat exchange elements when the catheter body 12 is positioned in the bloodstream and coolant is being circulated through the catheter, to exchange heat with the blood. In a preferred embodiment, the catheter body 12 is configured for placement within the venous system, preferably in the superior vena cava or inferior vena cava through the jugular vein or subclavian vein or femoral vein. Less preferably the catheter body 12 may be positioned in the arterial system.

Preferred non-limiting uses for the catheter body 12 include inducing mild or moderate therapeutic hypothermia in patients suffering a cardiac arrest, acute myocardial infarction, stroke, brain trauma, or undergoing aneurysm surgery. The catheter body 12 may also be used to rewarm such patients as well as rewarm patients post-surgery, e.g., post-cardiac bypass surgery. The preferred catheter body 12 also has, in addition to coolant lumens, one or more infusion lumens for, e.g., undertaking central venous line functions such as infusing medicaments into the patient 18 or monitoring, using one of the infusion lumens, characteristics of the patient 18.

To alleviate patient discomfort when the catheter body 12 is positioned against the skin 20 of the patient 18, an insulator 22 is provided. The insulator 22 is disposed between the catheter body 12 and the skin 20 so that when, for example, the catheter body 12 carries cold saline to cool a patient, the cold catheter body 12 will not lie directly on the skin 20 to cause the patient to shiver, which would otherwise complicate efforts to lower patient temperature. Preferred non-limiting examples of materials that can be used for the insulator 22 include thin insulating materials such as closed cell foam, paper, plastic, and fibrous materials.

Figure 2:
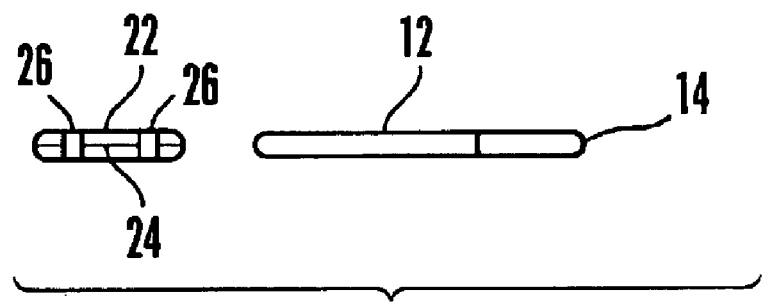
FIG. 2 is an exploded side view of the catheter with insulation.

In a non-limiting embodiment the insulator 22 is formed as flat sheet which is wrapped around the portion of the catheter body 12 that will contact the skin 20 when the catheter body 12 is properly advanced into the patient 18. Accordingly, when formed into what is essentially a cylindrical configuration as shown in FIG. 2, the insulator 22 has a slit or overlap 24. If desired, the insulator 22 can be held in the configuration shown in FIG. 2 by a Velcro® strap or straps 26, a hook element of each of which can be attached to one end of the sheet material of the insulator 22 and an eye element of which can be attached to the opposite end of the sheet material such that the two elements are juxtaposed with each other for easily engaging each other when the insulator 22 is placed in the cylindrical configuration shown, to hold the insulator 22 in that configuration. Other holders such as adhesive or ties, including suture thread, can be used in lieu of Velcro®.

In operation, the insulator 22 is wrapped around the portion of the catheter body 12 that will lie or that is lying against the skin of the patient. If provided, the holders are engaged with the insulator 22 to hold the insulator 22 in the configuration wherein it is wrapped around the catheter body 12. Cooling or heating of the patient can then be effected by circulating cold or hot coolant through the catheter body 12 and heat exchange element 14.

While the particular SYSTEM AND METHOD FOR INSULATING SKIN FROM INTRAVASCULAR HEAT EXCHANGE CATHETER as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". For example, the catheter body 12 might be advanced into a non-vasculature body orifice such as the rectum or bladder to effect heat exchange with the patient. All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. §112, sixth paragraph, unless the element is expressly recited using the phrase "means for" or, in the case of a method claim, the element is recited as a "step" instead of an "act".

What is claimed is:

1. A system comprising:

a closed loop heat exchange catheter configured for intravascular heat exchange with a human patient;

a source of heat exchange fluid in communication with the catheter; and an insulator configured for disposition between at least a portion of the catheter and the skin of the patient when the catheter is disposed in the vasculature of the patient, the insulator being formed with a slit along its length for receiving at least a portion of the catheter therethrough.

2. The system of claim 1, wherein the insulator is made of a sheet of thermally insulating material.

3. The system of claim 2, wherein the material is selected from the group consisting of closed cell foam, paper, plastic, and fibrous materials.

4. The system of claim 2, wherein the insulator is in a substantially cylindrical configuration when it is disposed between the catheter and the patient, and the system further includes at least one holder engaged with the insulator for holding the insulator in the substantially cylindrical configuration.

5. A method for treating a patient, comprising:

advancing a closed loop heat exchange catheter into the patient;

effecting heat exchange between the catheter and the patient; and thermally insulating the catheter from the patient's skin using at least one insulator lying against the skin of the patient between the catheter and the skin.

6. The method of claim 5, comprising wrapping the insulator around the catheter.

7. The method of claim 6, comprising holding the insulator in place as it is wrapped around the catheter.

8. The method of claim 5, wherein the catheter is disposed in the vasculature of the patient to exchange heat with blood flowing therethrough.

9. A system, comprising:

closed loop heat exchange means configured for placement in the vasculature of a patient to exchange heat with blood flowing in the vasculature; and insulating means for thermally insulating the catheter from the skin of the patient, wherein the insulating means is an insulator made of a material selected from the group consisting of closed cell foam, paper, and fibrous materials.

10. The system of claim 9, further comprising heat exchanger means for supplying heat exchange fluid to the closed loop heat exchange means.

11. The system of claim 9, further comprising holder means for holding the insulating means in engagement with the closed loop heat exchange means.

* * * * *